(12) United States Patent
McDonald

(10) Patent No.: US 6,398,277 B1
(45) Date of Patent: Jun. 4, 2002

(54) CONTACT LENS INSERTION DEVICE

(76) Inventor: Marguerite B. McDonald, 2858 Chestnut St., New Orleans, LA (US) 70115

( * ) Notice: Subject to any disclaimer, the term of this patent is extended or adjusted under 35 U.S.C. 154(b) by 0 days.

(21) Appl. No.: 09/805,878

(22) Filed: Mar. 15, 2001

(51) Int. Cl.⁷ .................................................. A61F 9/00
(52) U.S. Cl. ...................................................... 294/1.2
(58) Field of Search ................................ 294/1.2, 64.1; 606/107; 206/5.1

(56) References Cited

U.S. PATENT DOCUMENTS

| | | | |
|---|---|---|---|
| 2,224,575 A | * 12/1940 | Montalvo-Guenard | 294/64.1 |
| 2,379,629 A | * 7/1945 | Eweson | 294/1.2 |
| 3,424,486 A | * 1/1969 | Corley | 294/1.2 |
| 3,879,076 A | * 4/1975 | Barnett | 294/1.2 |
| 4,113,297 A | 9/1978 | Quinn | |
| 4,123,098 A | 10/1978 | Shoup | |
| 4,479,672 A | 10/1984 | Jermyn | |
| 4,565,396 A | * 1/1986 | Larimer | 294/1.2 |
| 5,538,301 A | 7/1996 | Yavitz et al. | |
| 5,941,583 A | 8/1999 | Raimondi | |

FOREIGN PATENT DOCUMENTS

| | | | | |
|---|---|---|---|---|
| FR | 2611-563 | * | 9/1988 | 294/64.1 |

* cited by examiner

*Primary Examiner*—Dean J. Kramer
(74) *Attorney, Agent, or Firm*—Locke Liddell & Sapp LLP

(57) ABSTRACT

A contact lens insertion device includes a syringe having a barrel and a piston slidably disposed within the barrel. The barrel is adapted for receiving a fluid which is drawn into the barrel and dispensed from the barrel through operation of the piston. A cup is attached to the syringe. The cup includes a concave surface adapted to receive a contact lens therein. The cup further includes a chamber in fluid communication with the syringe barrel. The concave surface of the cup includes an aperture in communication with the chamber, such that fluid or gel flows from the barrel through the chamber and cup aperture upon actuation of the piston to force the fluid or the gel to flow out of the cup aperture to thereby eject the contact lens from the cup.

1 Claim, 1 Drawing Sheet

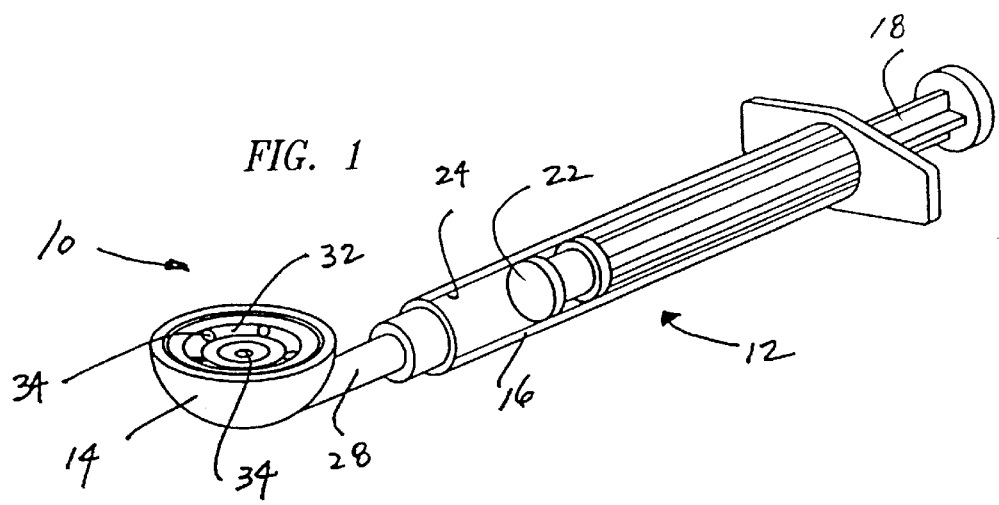
FIG. 1
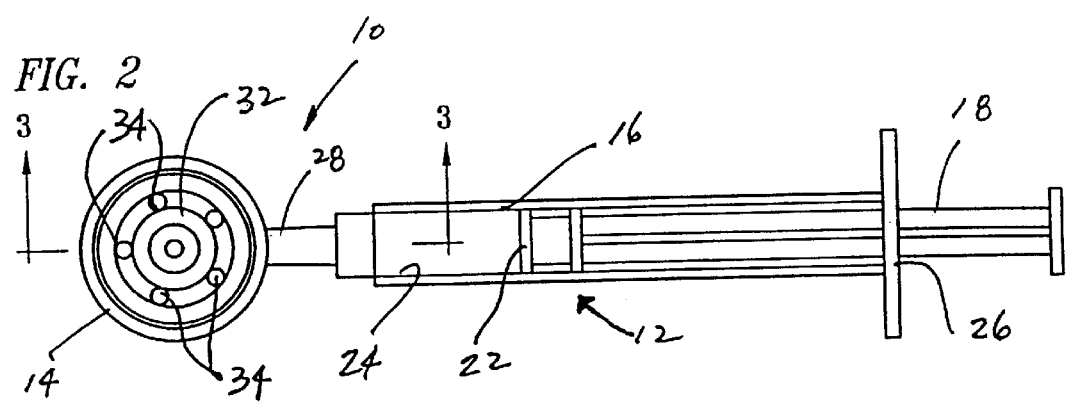
FIG. 2
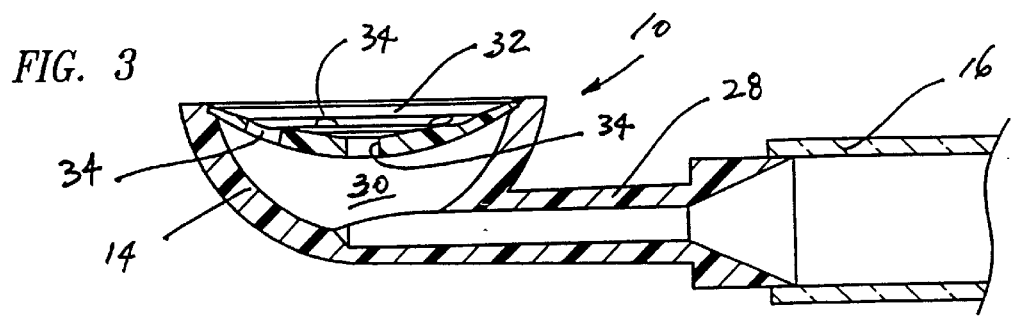
FIG. 3
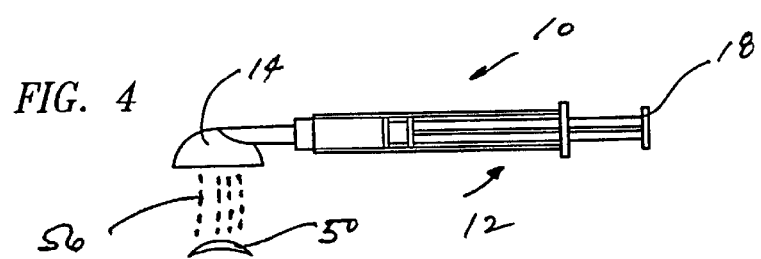
FIG. 4

CONTACT LENS INSERTION DEVICE

TECHNICAL FIELD OF THE INVENTION

The present invention relates to contact lenses, and more particularly to a device for inserting bandage contact lenses into a patient's eye to minimize contamination of and damage to the contact lens and to shorten the insertion time.

BACKGROUND OF THE INVENTION

Bandage contact lenses are often applied following eye surgery (or eye injury) to cover and protect the corneal area. The lens is normally applied by a ophthalmic surgeon as part of a surgical procedure. Previous procedures have required a surgical assistant to remove a lens from a blister pack. Sterile sponges are used to maneuver the lens first onto the sponge, which is then passed to a surgeon who applies the lens to the patient's eye. Since the lens is extremely thin, handling the lens may cause the lens to fold, and stick to itself. Efforts to unfold the lens can waste time and can damage the lens, rendering it unusable. Efficient insertion methods are thereby required which will not cause damage to a lens or injure the eye of a patient.

Therefore, a need has arisen for a contact lens insertion device that is easy to operate and which minimizes contamination of and damage to the contact lens.

SUMMARY OF THE INVENTION

In accordance with the present invention, a contact lens insertion device is provided that includes a syringe having a barrel and a piston slidably disposed within the barrel. The barrel is adapted for receiving a fluid which is drawn into the barrel and dispensed from the barrel through operation of the piston. A cup is attached to the syringe. The cup includes a concave surface adapted to receive a contact lens therein. The cup further includes a chamber in fluid communication with the syringe barrel. The concave surface of the cup includes an aperture in communication with the chamber, such that fluid flows from the barrel through the chamber and cup aperture upon actuation of the piston to force fluid to flow out of the cup aperture to thereby eject the contact lens from the cup and onto the surface of the eye.

BRIEF DESCRIPTION OF THE DRAWINGS

For a more complete understanding of the present invention and for further advantages thereof, reference is now made to the following Description of the Preferred Embodiments taken in conjunction with the accompanying Drawings in which:

FIG. 1 is a perspective view of the present insertion device;

FIG. 2 is a top plan view of the present insertion device illustrated in FIG. 1;

FIG. 3 is a cross-sectional view taken generally along section lines 3—3 of FIG. 2; and FIG. 4 illustrates a contact lens being ejected from the cup of the present insertion device into an eye.

DESCRIPTION OF THE PREFERRED EMBODIMENTS

Referring simultaneously to FIGS. 1–3, the present contact lens insertion device is illustrated, and is generally identified by the numeral 10. As used herein, the term contact lens includes lenses of any material or color and with and without correction. Insertion device 10 includes a syringe, generally identified by the numeral 12. Syringe 12 includes a cup 14 which is adapted to receive a contact lens (not shown). Cup 14 may be fabricated from any material; for example, steel or plastic materials. Syringe 12 is of a conventional design and includes a barrel 16 and a piston 18. Piston 18 is adapted to reciprocatingly slide within barrel 16 to alternately draw fluid within barrel 16 and force fluid from barrel 16.

Piston 18 includes a head 22 which creates a fluid-tight seal against the entire circumference of the inside surface 24 of barrel 16 for preventing fluid from leaking out of end 26 of barrel 16. Fluid disposed within barrel 16 of syringe 12 may be, for example, water, a saline solution, a balanced salt solution, or a gel.

Cup 14 is attached to a tip 28 of syringe 12. Tip 28 of syringe 12 may include, for example, a Luer lock connector with an Archimedes screw for attachment to cup 14. Any type of interference fit connection may be utilized for attaching tip 28 to cup 14. Cup 14 includes a chamber 30 in fluid communication via tip 28 with barrel 16. Cup 14 includes a concave surface 32 upon which a contact lens is placed. Surface 32 includes a plurality of apertures 34 which communicate with chamber 30. By operation of piston 18, fluid is ejected from barrel 16 into chamber 30 of cup 14, and fluid exits chamber 30 via apertures 34.

Referring now to FIG. 4, in operation of the present insertion device 10, a contact lens 50 to be inserted or deposited into an eye 52 is positioned within cup 14 on surface 32 after barrel 16 of syringe 12 has been filled with a desired fluid. Piston 18 of syringe 12 is activated a by physician following a surgical procedure to expel fluid 56 from barrel 16 of syringe 12, thereby ejecting contact lens 50 from cup 14 so that contact lens 50 washes quickly and gently onto eye 52 in the proper unfolded condition and in the proper orientation. As shown in FIG. 4, when in use, insertion device 10 is inverted so that cup 14 is pointing toward the eye 52. Lens 50 is retained within cup 14 by surface tension due to the wetting of surface 32 of cup 14. Thus, lens 50 will not be ejected from device 10 until a sufficient amount of water is ejected from barrel 16.

Lens 50 may be pre-packaged with insertion device 10 in a sterile package with the barrel of the insertion device loaded with a fluid or gel, and lens 50 disposed within cup 14. A surgeon would simply remove device 10 from the sterile package and be ready to insert lens 50.

It therefore can be seen that the present invention provides for a contact lens insertion device which does not require the user to directly contact the lens nor require excessive lens manipulation nor wasted time during insertion of the lens.

Whereas the present invention has been described with respect to specific embodiments thereof, it will be understood that various changes and modifications will be suggested to one skilled in the art and it is intended to encompass such changes and modifications as fall within the scope of the appended claims.

What is claimed is:

1. A contact lens insertion device comprising:
   a syringe including a barrel and a piston slidably disposed within said barrel to alternately draw fluid within said barrel and evacuate fluid from said barrel;
   said fluid is selected from the group consisting of water, a saline solution, a balanced salt solution, and a gel;
   a cup attached to said syringe, said cup including a concave surface adapted to receive a contact lens therein, a contact lens being retained within said cup by surface tension created by said fluid; and said cup further including a chamber in fluid communication with said barrel, said concave surface of said cup including a plurality of apertures in fluid communication with said chamber, such that upon actuation of said piston to evacuate fluid from said barrel of said syringe, fluid is expelled from said plurality of apertures to overcome the surface tension retaining a contact lens on said concave surface and thereby eject a contact lens disposed on said concave surface of said cup.

* * * * *